(12) United States Patent
Keegan et al.

(10) Patent No.: US 7,601,126 B2
(45) Date of Patent: Oct. 13, 2009

(54) LAMENESS EVALUATION SYSTEMS AND METHODS

(75) Inventors: Kevin G. Keegan, Columbia, MO (US); Perngjin Frank Pai, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 11/780,881

(22) Filed: Jul. 20, 2007

(65) Prior Publication Data

US 2008/0021352 A1 Jan. 24, 2008

Related U.S. Application Data

(60) Provisional application No. 60/832,424, filed on Jul. 21, 2006.

(51) Int. Cl.
*A61B 5/103* (2006.01)
*G08B 23/00* (2006.01)
*G01R 23/00* (2006.01)

(52) U.S. Cl. .................. 600/595; 340/573.7; 702/75
(58) Field of Classification Search ............... 600/595; 340/573.7; 702/75
See application file for complete search history.

(56) References Cited

U.S. PATENT DOCUMENTS

| | | | | |
|---|---|---|---|---|
| 3,999,611 A | * | 12/1976 | Bucalo | 168/4 |
| 4,233,845 A | * | 11/1980 | Pratt, Jr. | 73/865.4 |
| 4,774,679 A | * | 9/1988 | Carlin | 702/41 |
| 4,935,887 A | | 6/1990 | Abdalah et al. | |
| 5,138,550 A | * | 8/1992 | Abraham et al. | 340/573.7 |
| 5,369,601 A | * | 11/1994 | Tannenbaum | 702/139 |
| 6,301,964 B1 | * | 10/2001 | Fyfe et al. | 73/510 |
| 6,699,207 B2 | | 3/2004 | Tasch et al. | |
| 2002/0107649 A1 | * | 8/2002 | Takiguchi et al. | 702/75 |
| 2003/0135097 A1 | * | 7/2003 | Wiederhold et al. | 600/301 |
| 2003/0139692 A1 | * | 7/2003 | Barrey et al. | 600/595 |
| 2004/0077975 A1 | | 4/2004 | Zimmerman | |
| 2006/0000420 A1 | | 1/2006 | Martin Davies | |
| 2007/0000216 A1 | * | 1/2007 | Kater et al. | 54/1 |

OTHER PUBLICATIONS

Buchner et al., "Head and trunk movement adaptations in horses with experimentally induced fore-or hindlimb lameness". Equine vet. J. (1996) 28, pp. 71-76.*
Buchner et al., "Limb movement adaptations in horses with experimentally induced fore-or hindlimb lameness". Equine vet. J. (1996) 28, pp. 63-70.*

(Continued)

*Primary Examiner*—Max Hindenburg
*Assistant Examiner*—Sean P Dougherty
(74) *Attorney, Agent, or Firm*—Robert O. Enyard, Jr.; Polsinelli Shughart PC

(57) ABSTRACT

A wireless sensor-based lameness evaluation system detects and analyzes patterns of vertical head and pelvic motion of a four-legged animal in correlation with at least one limb movement. The system includes a plurality of motion sensors attached to the head, pelvis (or along the center of the back), and at least one limb of the animal. A processing system in receives the motion data and processes the motion data to detect and quantify forelimb and/or hindlimb lameness in the animal.

39 Claims, 14 Drawing Sheets

OTHER PUBLICATIONS

Vorstenbosch et al., "Modeling study of compensatory head movements in lame horses". Am J Vet Res. (1997) 58, pp. 713-718.*

Mayagoita et al., "Accelerometer and rate gyroscope measurement of kinematics: an inexpensive alternative to optical motion analysis systems". J Biomechanics. (2002) 35, pp. 537-542.*

K. Keegan et al., Detection of lameness and determination of the affected forelimb in horses by use of continuous wavelet transformation and neural network classification of kinematic data, Nov. 2003, pp. 1376-1381, AJVR, vol. 64, No. 11.

K. Keegan et al., Accelerometer-Based System for the Detection of Lameness in Horses, Biomedical Sciences Instrumentation, 2002, pp. 107-112, 38 (ISA [International Society for Measurement and Control] vol. 419).

K. Keegan et al., Evaluation of a sensor-based system of motion analysis for detection and quantification of forelimb and hind limb lameness in horses, May 2004, pp. 665-670, AJVR, vol. 65, No. 5.

K. Keegan et al., Signal decomposition method of evaluating head movement to measure induced forelimb lameness in horses trotting on a treadmill, pp. 446-451, 2001, Equine Veterinary Journal.

K. Keegan et al., A curve-fitting technique for evaluating head movement to measure forelimb lameness in horses, Biomedical Sciences Instrumentation, 2000, pp. 239-244, 36 (ISA [International Society for Measurement and Control] vol. 395).

International Search Report and Written Opinion for PCT/US07/74014 dated Jul. 3, 2008 (8 pages).

* cited by examiner

FIG. 4A
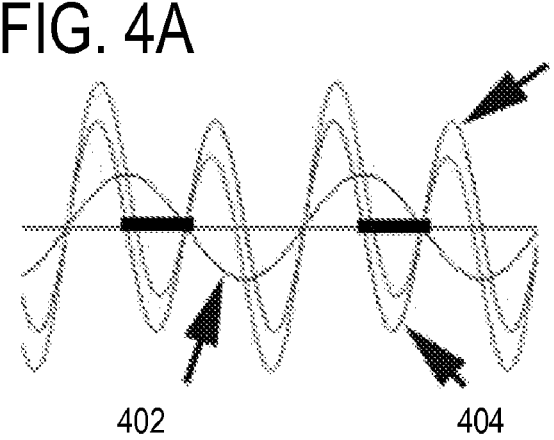
402   404
FIG. 4B
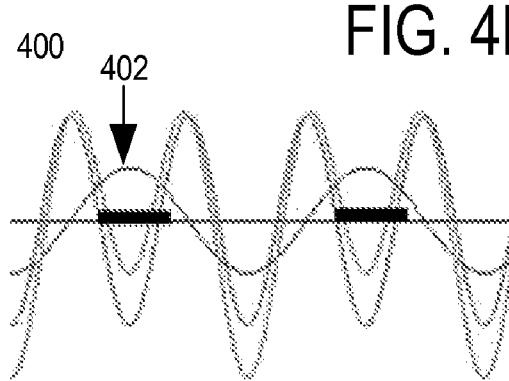
400  402
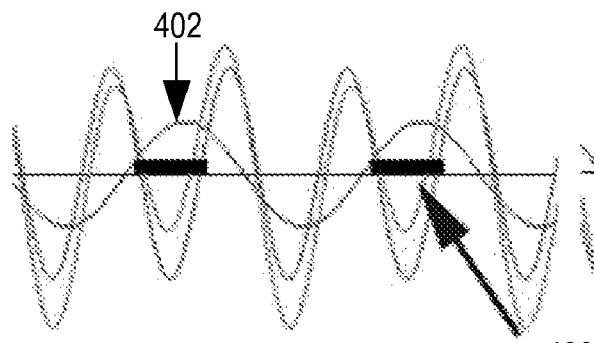
402
FIG. 4C    406
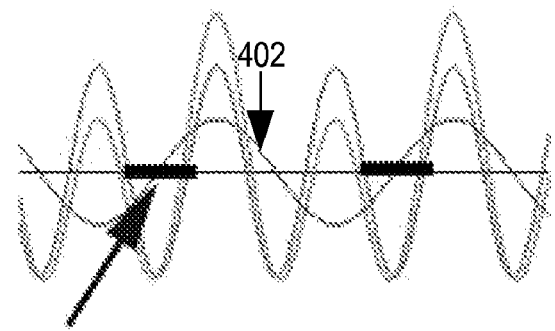
402
FIG. 4D

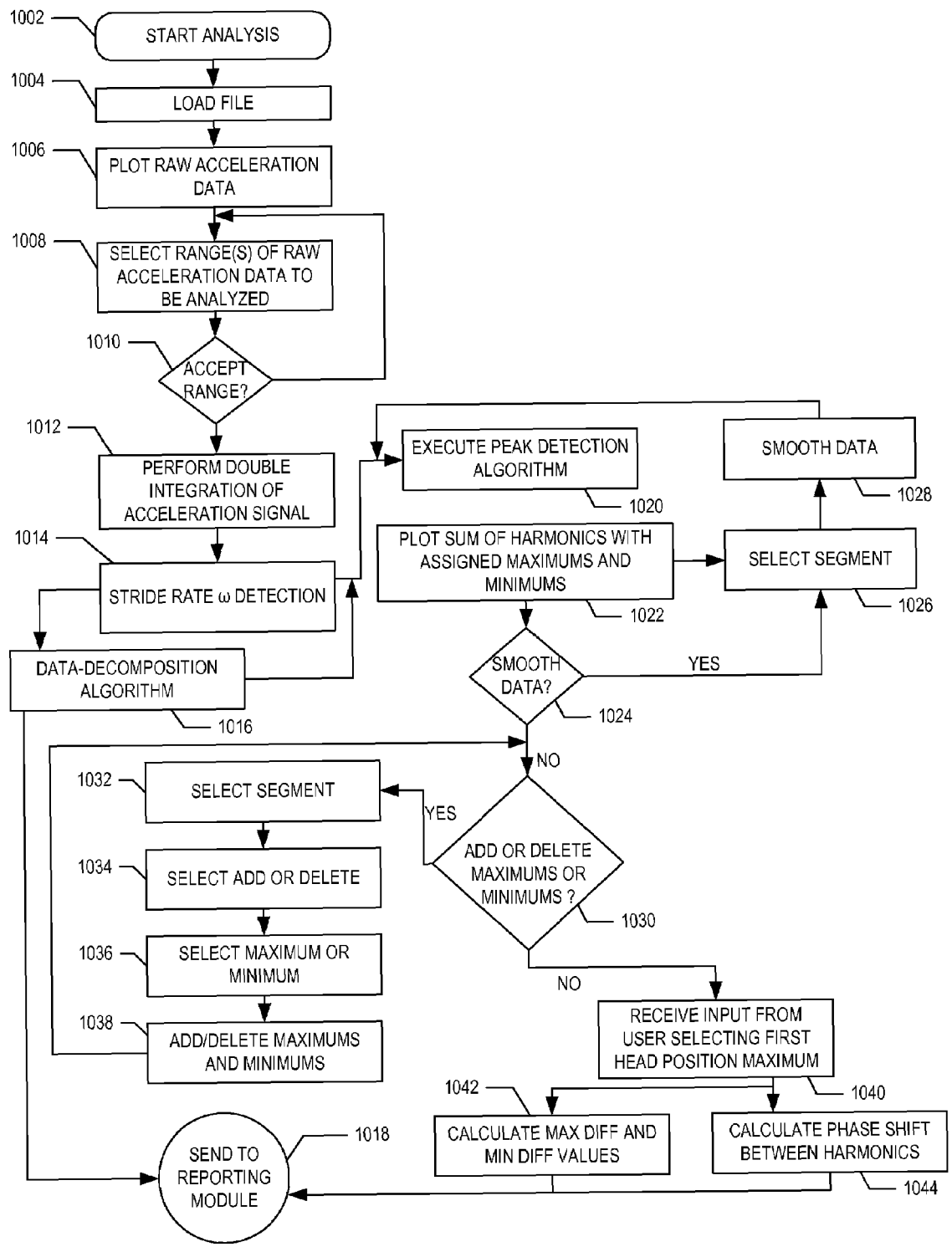

LAMENESS EVALUATION SYSTEMS AND METHODS

RELATED APPLICATIONS

This application claims priority to U.S. Provisional Application No. 60/832,424, entitled Wireless, Sensor-Based Lameness Evaluation System, filed Jul. 21, 2006, the entire contents of which are incorporated herein by reference.

FEDERALLY SPONSORED RESEARCH OR DEVELOPMENT

Not applicable.

COMPACT DISK APPENDIX

Not applicable.

BACKGROUND

Lameness is the single most common medical condition affecting horses, resulting in an estimated 600 million to one billion dollar annual loss to the horse-owning public. Typically, lameness evaluation in horses is performed primarily by subjective visual evaluation. For example, an equine practitioner will look at how a horse's head or pelvis moves during a trot to detect and/or diagnose lameness. However, lameness of mild severity can be confusing, and the agreement for subjective evaluation even between experts is poor.

Currently, certain methods and systems have been developed in attempting to achieve more objective evaluation of lameness, but only with limited success. For example, motion analysis systems for detection of lameness in horses, with numerous descriptions, using high-speed video camera, are commercially available. For example, U.S. Pat. No. 6,699,207 to Tasch et al. describes a method of using stationary force plates for the detection and evaluation of horse and cattle lameness. Lameness quantification based upon frequency-based head and pelvic motion has also been investigated.

Another lameness evaluation system developed in France involves the use of accelerometers on the torso to collect body motion data. A fiber optic-based system with wireless data transmission for the visualization of equine movement has been commercially available from Equine Performance Technologies, Inc., located in Oldwich, N.J. However, all of the above mentioned methods and systems are either difficult to implement in the field, expensive, or encumber the natural movement of the horse with excessive or heavy equipment. In addition, although they allow sophisticated data collection, none provide lameness-specific data analysis.

Horses with forelimb lameness will show a "head nod" (or "head bob"), which can be described as the horse's head moving upward during the weight bearing phase of the lame limb and downward during the weight bearing phase of the sound limb. Indeed, this is what actually happens in horses with severe forelimb lameness and what appears to happen to the naked eye during the trot in horses with mild to moderate forelimb lameness. However, due to the rapid movement of the limbs in a horse and the limited temporal resolution of the human eye, these descriptions of the "head nod" are too simple and not entirely correct. Similarly, "hip hike," "hip drop," and "gluteal rise" are terms frequently used to describe hindlimb lameness in horses, but these descriptions are also imprecise and incomplete. Objective measurements of head and pelvic movement in lame horses have been made in some laboratory-based, experimental studies.

Therefore, it is desirable to provide a lameness detection and quantification method/system that can measure and evaluate the patterns of vertical head and pelvic motion in correlation with vertical feet movement to detect and quantify lameness in horses. It is also most desirable to provide a method and system to the practicing equine veterinarian in the field that helps in the determination of the specific cause of lameness in a horse.

SUMMARY

In one aspect, methods and systems detect lameness in animals, including four-legged animals, and promote health of the animals. One system includes a sensor-based diagnostic data retrieving and analyzing system that enables a user to evaluate the patterns of vertical head and pelvic motion of a four-legged animal in correlation with its vertical feet movement to detect and quantify forelimb and hindlimb lameness.

According to another aspect, a system evaluates lameness in an animal. The system comprises a plurality of motion sensors configured to generate a corresponding plurality of signals comprising motion data representative of a head motion, a pelvis motion, and at least one limb motion during a stride of the animal. The system further includes a processing system configured to receive the plurality of signals during the stride via wireless communication and to receive input data. The processing system comprises an evaluation application that comprises executable modules. A data-acquisition module is configured to retrieve motion data from the received plurality of signals. A data-decomposition module is configured to generate a simulated vertical head movement pattern and a simulated pelvis movement pattern for the stride. A curve-modification module is configured to modify and smooth the simulated vertical head and pelvis movement patterns based on the input data received from a user via a user-interactive interface. A position-detection module is configured to detect a maximum head position, a minimum head position, a maximum pelvis position, and a minimum pelvis position during the stride based on modified simulated head and pelvis movement patterns. A phase-shift calculation module is configured to identify a limb affected with lameness and to determine a type of the lameness in the identified limb based on a comparison of the detected maximum head position, the detected minimum head position, the detected maximum pelvis position, and the detected minimum pelvis position with at least one lameness reference pattern, the at least one lameness reference pattern indicating a peak time of lameness.

According to another embodiment, an evaluation system evaluates lameness in an animal and is operable with at least one processor. The evaluation system is configured to receive a plurality of signals comprising motion data representative of a head motion, a pelvis motion, and at least one limb motion during a stride of the animal. The evaluation system comprises executable modules. A data-acquisition module is configured to collect motion data from the received plurality of signals. A data-decomposition module is configured to generate simulated head and pelvis movement patterns for the stride. A curve-modification module is configured to receive input data and to modify and smooth the simulated head and pelvis movement patterns based on the input data. A position-detection module is configured to detect a maximum head position, a minimum head position, a maximum pelvis position, and a minimum pelvis position during the stride based on the modified simulated head and pelvis movement patterns. A phase-shift calculation module is configured to identify a limb affected with lameness based on a comparison of the detected maximum head position, the detected minimum head position, the detected maximum pelvis position, and the detected minimum pelvis position with at least one lameness reference pattern. The lameness reference pattern indicates a peak time of lameness.

According to another aspect, a computerized method evaluates lameness in a four-legged animal. The method comprises generating a plurality of signals representative of a motion of a head, a pelvis, and at least one limb during a stride of the animal. The method further comprises receiving the plurality of signals via wireless communication at a processing system for processing. Motion data is collected from the received plurality of signals. A stride rate detection method automatically selects segments of the motion that are good for detecting lameness. Simulated head and pelvis movement patterns are generated for the stride. Automatic and user-controlled peak finding and elimination methods optionally may be received. As input data, and calculations are automatically initiated based on automatically selected time indices of the received input data. A maximum head position, the detected minimum head position, the detected maximum pelvis position, and the detected minimum pelvis position are detected in the stride and comparison to lameness reference patterns and a limb affected with lameness is identified in the stride base on an analysis of the detected maximum head position, and the detected minimum pelvis position in the stride and comparison to lameness reference patterns. In one aspect, the reference patterns are previously measured in the laboratory and on animals with natural lameness, the reference lameness patterns indicating peak time of lameness.

According to another aspect, a computerized method evaluates lameness in a four-legged animal. The method comprises receiving motion data representing a plurality of strides of the animal from a plurality of motion sensors attached to a head, a pelvis, and at least one limb of animal. The received motion data is processed to identify at least two harmonic components and at least one transient component. Simulated vertical head and vertical pelvis movement patterns are generated based on the identified two harmonics and the at least one transient component data. A vertical head movement and a vertical pelvic movement are correlated with a vertical forelimb or hindlimb movement to identify the affected limb or limbs. A phase shift is calculated between the at least two harmonic components to detect a type of lameness suffered by the animal.

BRIEF DESCRIPTION OF THE DRAWINGS

FIGS. 4A-4D illustrate four reference patterns of head movement due to forelimb lameness.

FIG. 10 is a flow chart illustrating a detailed data analysis method in accordance with an aspect of a lameness evaluation system.

DETAILED DESCRIPTION

Aspects of the lameness evaluation systems and methods described herein detect and analyze lameness in animals using sensor-based diagnostics. One advantage of the systems is their ability to objectively quantify lameness in the field, especially in diagnosing lameness of mild severity or involving multiple limbs. One technique quantifies lameness using data collected from several contiguous strides or movement by a four-legged animal so lameness variability over short periods of time can be studied and controlled. Furthermore, the systems can be deployed in any environment, are not limited to laboratory treadmills, and are more portable and cost effective than current commercial systems.

Figure 1A:
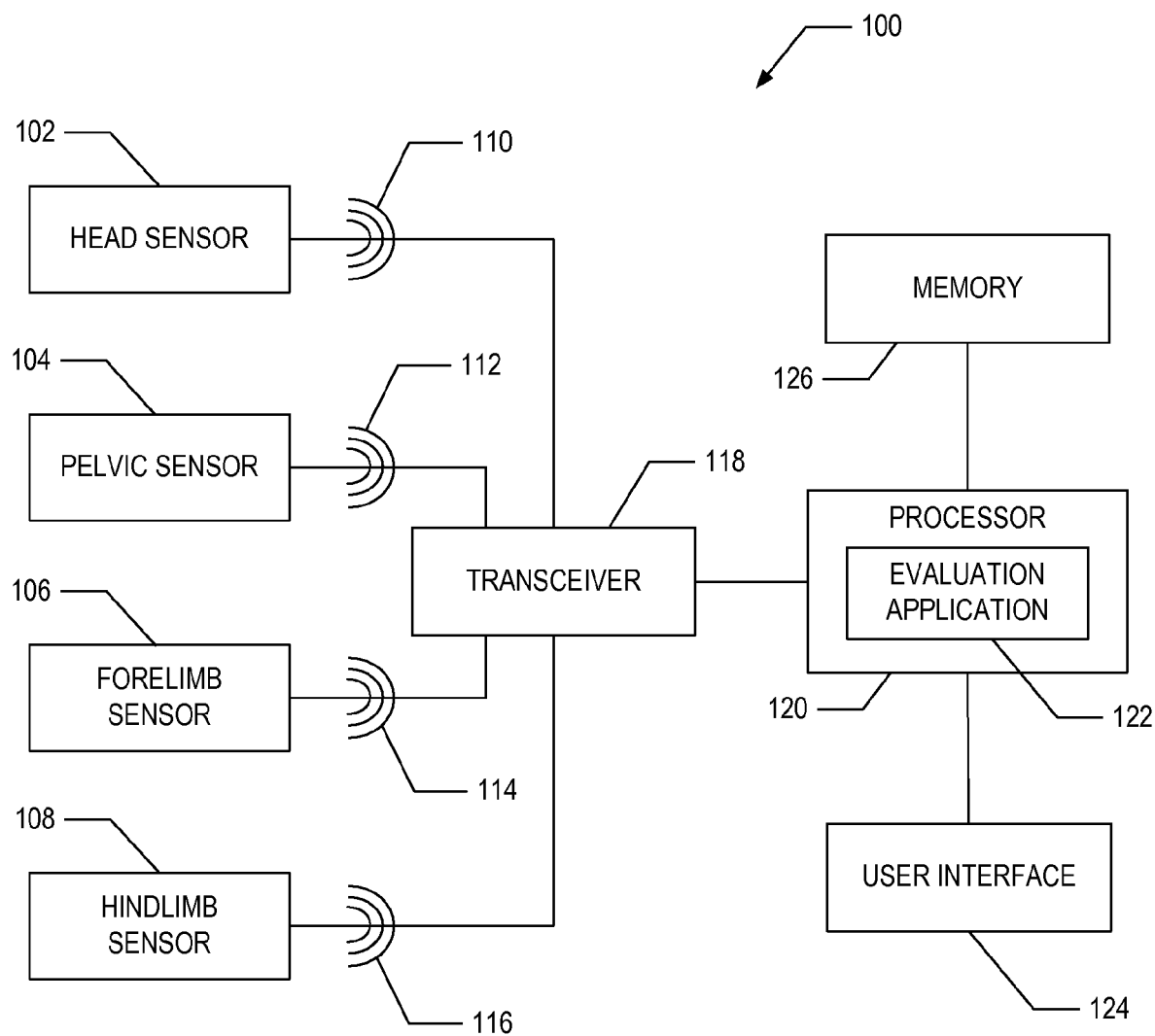
FIG. 1A is a block diagram of a lameness evaluation system in accordance with an aspect of the present invention.

FIG. 1A depicts an exemplary aspect of a lameness evaluation system 100. The evaluation system 100 detects and analyzes the patterns of vertical head and pelvic motion of an animal, such as a four-legged animal, in correlation with its feet movement to identify and quantify lameness.

A head sensor 102 and a pelvic sensor 104 are outfitted on the head and the pelvis (or along the center of the back), respectively, of the animal. The head sensor 102 and pelvic sensor 104 are motion sensors, such as accelerometers, that obtain motion data relative to the head and pelvis during a period of trotting or walking gait (i.e., during a stride) of the animal. The motion data sensed by the head sensor 102 and the pelvic sensor 104 is referred to herein as acceleration data.

In one aspect, a forelimb sensor 106 and a hindlimb sensor 108 are outfitted on the bottom part of a forelimb (e.g., forefoot) and the bottom part of a hindlimb (e.g., hindfoot), respectively, of the animal. In another aspect, the sensors 106-108 may be outfitted on other parts of the limbs.

The forelimb sensor 106 and the hindlimb sensor 108 are motion sensors, such as gyroscopes, that obtain motion data relative to the limb during the period of trotting or walking gait by the animal. The motion data sensed by the forelimb sensor 106 and the hindlimb sensor 108 is referred to herein as limb angular velocity data or gyroscopic data.

According to one aspect, the forelimb sensor 106 and the hindlimb sensor 108 are attached to the same side of the animal. For example, if the forelimb sensor 106 is attached to the right forefoot, the hindlimb sensor 108 is attached to the right hindfoot.

Each of the motion sensors 102-108 are configured to generate a signal that comprises motion data representative of motion sensed at the location of the animal to which the sensor is outfitted. For example, the head sensor 102 generates a first signal 110 comprising motion data representative of a head motion. The pelvic sensor 104 generates a second signal 112 comprising motion data representative of a pelvis motion. The forelimb sensor 106 generates a third signal 114 comprising motion data representative of a forelimb motion. The hindlimb sensor 108 generates a fourth signal 116 comprising motion data representative of hindlimb motion. Moreover, each of the sensors 102-108 are configured to transmit the generated signals, including by wireless and/or wired communication.

A transceiver 118 receives the generated signals 110-116 and transmits the received signals 110-116 to a processing system 120 for processing. In one aspect, the transceiver 118 receives the signals 110-116 emitted from the sensors 102-108, respectively, via a wireless communication link, and transmits the signals 110-116 to the processing system 120 via a wireless communication link. An antenna (not show) may be included within the transceiver 118.

The processing system 120 includes one or more processors or processing systems and employs a software subsystem, or a software application, to process the motion data included in the received signals 110-116. For example, the processing system 120 executes a lameness evaluation application 122 to process the received motion data and to objectively detect and diagnose lameness in the animal. The processing system 120 includes a transceiver (not shown) that receives the signals 110-116 from the transceiver 118. In one aspect, the transceiver for the processing system 120 is a wireless transceiver configured to receive wireless communication signals.

In one aspect, the processing system 120 is a remote computer, such as a laptop computer or a personal computer station. In another aspect, the processing system 120 is a server computer. In another aspect, the processing system 120 communicates with the transceiver 118 via a wireless area communication network. In other aspects, other wireless and/or wired communications may be used.

A user interface (UI) 124 enables a user to input or manipulate motion data and to issue processing commands. Processing commands comprise, for example, commands to initiate data acquisition and/or commands to initiate data analyses. In one embodiment, the UI 124 includes a display, such as a computer monitor, for viewing motion data and an input device, such as a keyboard or a pointing device (e.g., mouse, trackball, pen, touch pad, or other device), for interacting with the motion data. The UI 112 generates one or more input forms for display via the display. The input forms enable the user, for example to select motion data for viewing and/or editing.

According to one aspect, the processing system 120 is coupled to a memory 126 for storing motion data for a particular animal, including processed and/or raw motion data. For example, the memory 126 comprises one or more files each comprising processed and/or raw motion data for a particular animal.

Figure 1B:
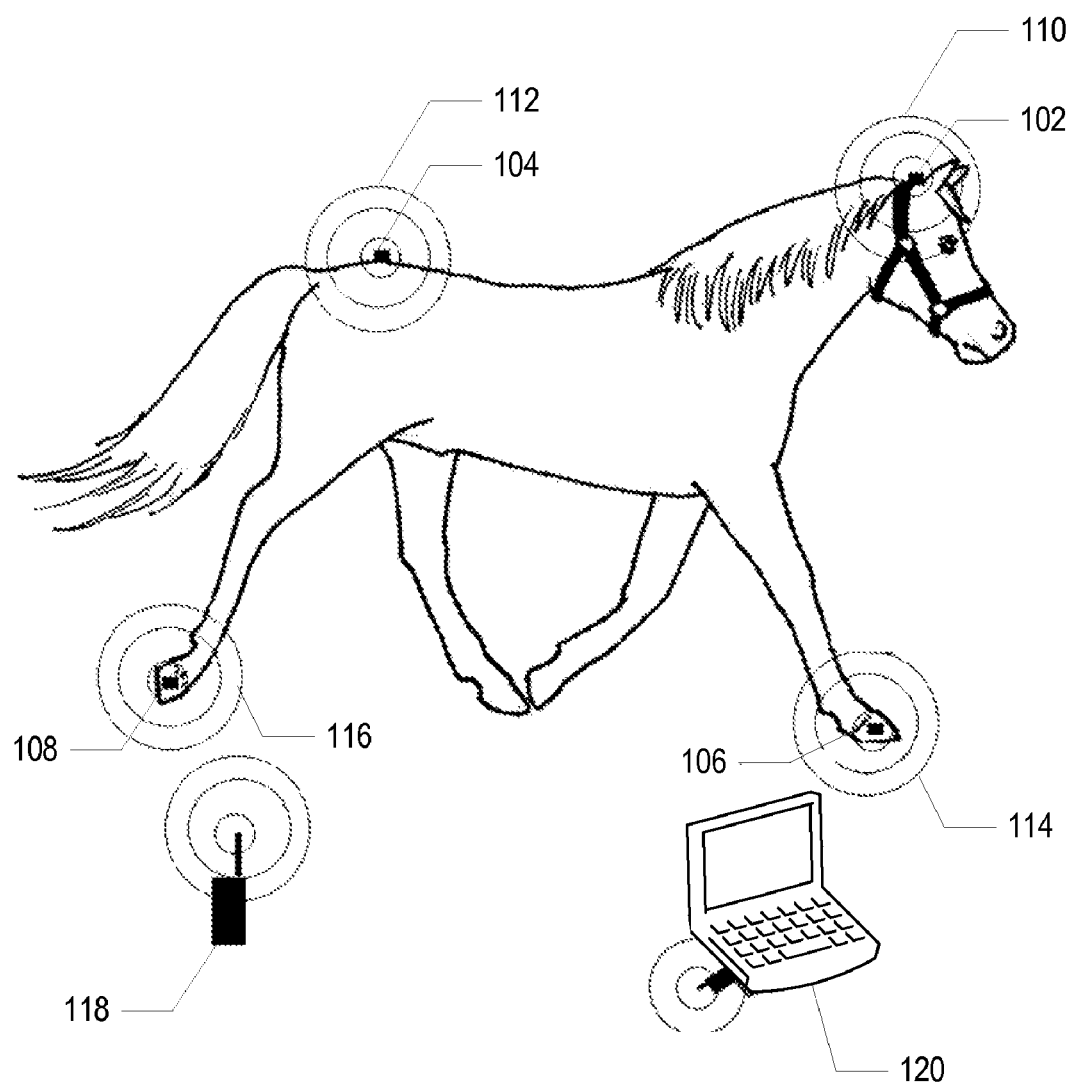
FIG. 1B depicts an exemplary operating environment in which the lameness evaluation system of FIG. 1A may be implemented.

FIG. 1B illustrates an aspect of the evaluation system 100 outfitted on a horse 130. The head sensor 102 and pelvic sensor 104 are depicted as being attached to the head and the pelvis, respectively. The forelimb sensor 106 and the hindlimb sensor 108 are attached to the forelimb and the hindlimb of the horse, respectively, such as on the horse's right feet. FIG. 1B further illustrates the transceiver 118 that receives signals 110-116 from the sensors 102-108 and that transfers the received signals 110-116 to the processing system 120, such as a portable computer. While it is contemplated that the sensors 102-108 may include multiple types of motion sensors, in one embodiment, the head sensor 102 and the pelvic sensor 104 are accelerometers, while the forelimb sensor 106 and the hindlimb sensor 108 are gyroscopes.

Figure 1C:
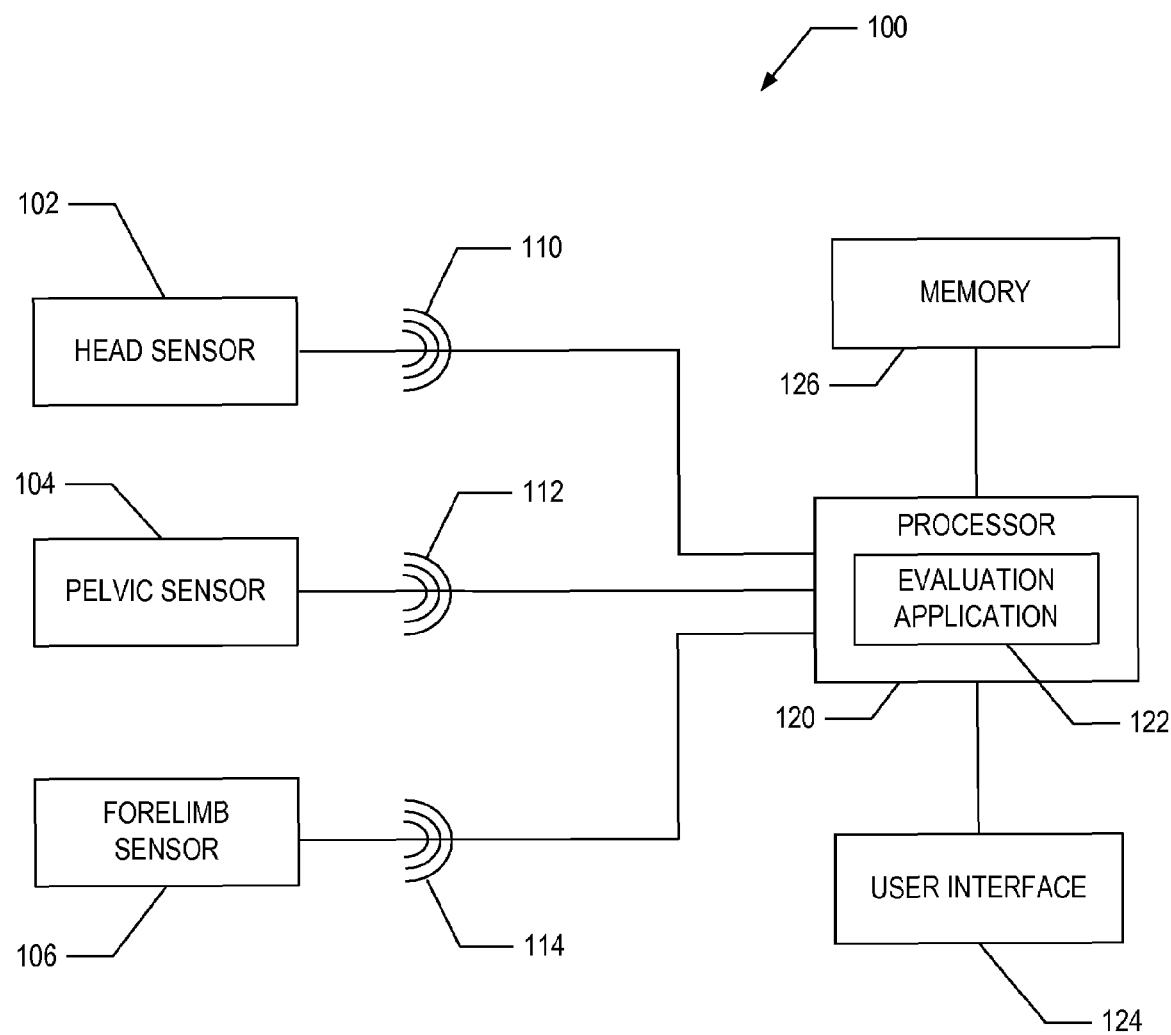
FIG. 1C is a block diagram of a lameness evaluation system in accordance with another aspect of the present invention.

FIG. 1C depicts another exemplary aspect of an evaluation system 100. According to this aspect, the evaluation system 100 includes a head sensor 102, a pelvic sensor 104, and a single limb sensor, such as the forelimb sensor 106.

Figure 1D:
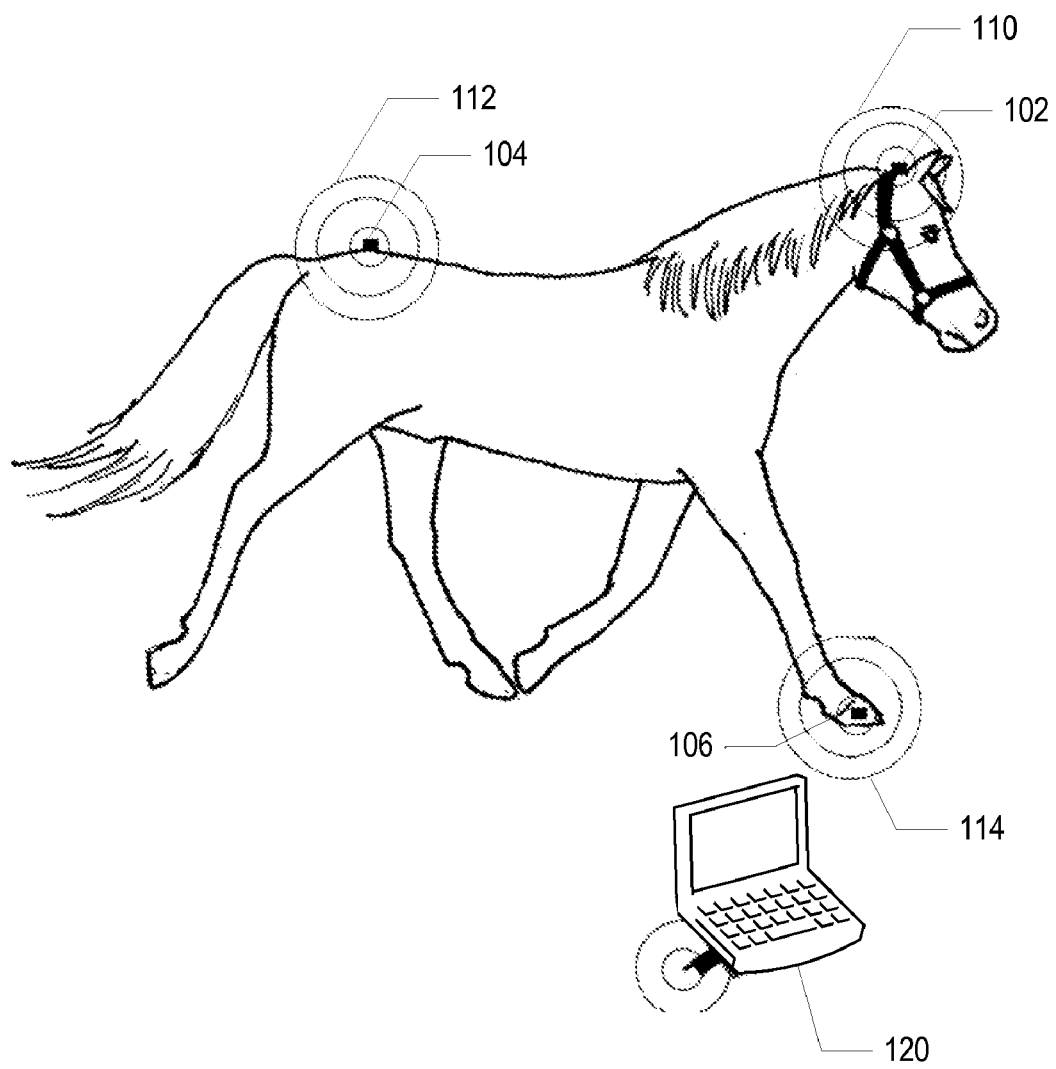
FIG. 1D depicts an exemplary operating environment in which the lameness evaluation system of FIG. 1C may be implemented.

Moreover, the processing system 120 depicted in FIG. 1C is configured to receive the generated signals 110-114 directly from the sensors 102-106. In this aspect, a separate intermediate transceiver, such as the transceiver 118, is not used. The processing system 120 then employs the evaluation application 122 to process the motion data included in the generated signals 110-114 to detect and quantify lameness. FIG. 1D illustrates an exemplary operating environment based on the evaluation system depicted in FIG. 1C.

Figure 2:
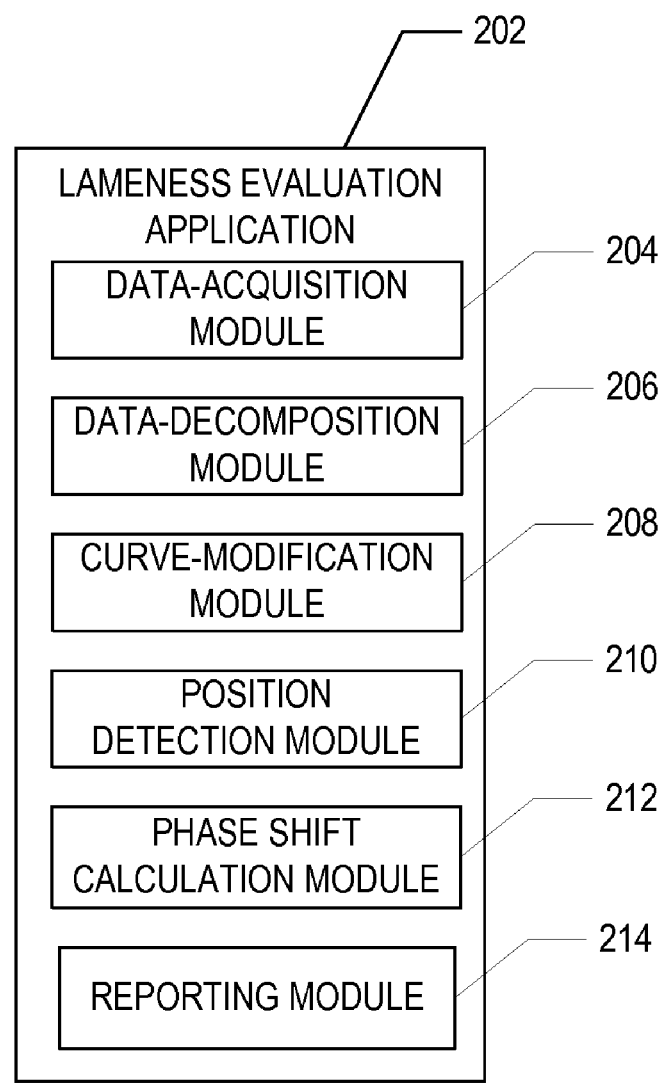
FIG. 2 is a block diagram of a lameness evaluation application according to one aspect of a lameness evaluation system.

FIG. 2 illustrates an exemplary evaluation application 202 (e.g., evaluation application 122) according to one aspect of the evaluation system 100. The evaluation application 202 comprises instructions or modules that enable a processing system (e.g., processing system 120) to process motion data and objectively detect and/or diagnose lameness.

A data-acquisition module 204 is configured to collect motion data for pre-determined but unrestricted time intervals. For example, the data-acquisition module 204 collects the motion data transmitted from the transceiver 118 for intervals during the period of trotting or walking gait. According to one aspect, the predefined interval is a default time period retrieved from a memory (e.g., memory 126). In one example, the predefined interval is a fixed period, such as ten minutes. According to another aspect, there is no predefined interval. For example, data-acquisition module 204 collects the motion data transmitted from the transceiver 118 for the entire period during which the animal is trotting or in walking gait.

In another aspect, the predefined interval is definable by a user. For example, prior to executing the application 202, a user uses the UI 124 to define a desired time interval for collecting motion data. In one example, the time interval is defined as ten minutes.

The data-acquisition module 204 is further configured to arrange the collected motion data into different data sets according to their generating locations, such as the head, pelvis, forelimb, or hindlimb foot. According to one aspect, the data-acquisition module 204 creates a motion data table that comprises motion data sensed by each of the sensors 102-108, and stores the created tables in the memory 126. For example, the data-acquisition module 204 creates a head motion table for storing motion data sensed by the head sensor 102, a pelvis motion table for storing motion data sensed by the pelvic sensor 104, a forelimb motion table for storing motion data sensed by the forelimb sensor 106, and optionally a hindlimb motion table for storing motion data sensed by the hindlimb sensor 108. For aspects that do not include a hindlimb sensor 108, a hindlimb motion table is not created.

A data-decomposition module 206 is configured to simulate the vertical head and vertical pelvic movement patterns in accordance with a respective forelimb and hindlimb movement (e.g., head vs. forefoot and pelvis vs. hindfoot) by integrating and decomposing the motion data. For aspects that do not include a hindlimb sensor 108, the data-decomposition module 206 is configured to simulate the vertical head and vertical pelvic movement patterns in accordance with forelimb movement. According to one aspect, the data-decomposition module 206 first performs a double integration of acceleration data from the head and pelvic sensors 102, 104 and calculates the stride rates from the gyroscopic data of the corresponding limb sensor (e.g., forefoot to head and hindfoot to pelvis). For aspects that do not include a hindlimb sensor 108, the data-decomposition module 206 first performs a double integration of acceleration data from the head and pelvic sensors 102, 104 and calculates the stride rates from the gyroscopic data of the forelimb sensor 106 (e.g., forefoot to head and forefoot to pelvis). The calculated stride rate indicates whether the animal is in a trotting phase or a walking gait phase.

According to another aspect, the data-decomposition module 206 further employs a curve-fitting algorithm (e.g., a Data-Decomposition Algorithm). The Data-Decomposition Algorithm assumes that the vertical head or pelvic movement (y(t)) can be described and simulated by three components: 1) a first harmonic component with frequency ω, describing unilateral lameness contribution to vertical head movement (ω=stride rate in strides/second), 2) a harmonic component with a frequency 2ω, describing the normal, biphasic, vertical head movement, and 3) a low-frequency, transient component describing extraneous vertical head or pelvic movement. Based on the above assumption, an animal's vertical head or pelvic movement can be mathematically expressed as $$y(\bar{t}) = C_1 \cos(\omega\bar{t}) + C_2 \sin(\omega\bar{t}) + C_3 \cos(2\omega\bar{t}) + C_4 \sin(2\omega\bar{t}) + C_5 + C_6\bar{t} + C_7\bar{t}^2 + C_8\bar{t}^3 \quad (1)$$

where $\bar{t} = t - t_m$ is a moving time coordinate and $t_m$ is the observed instant.

To find the coefficients $C_j$ (j=1, ... 8) for the data point at $\bar{t}=0$, the data points around $t=t_m$ are used to minimize the square error ($E_{rror}$), $$E_{rror} = \sum_{i=-N}^{N} \kappa_i (y_i - Y_i)^2 \quad (2)$$

where $y_i$ denotes $y(\bar{t}_i)$, $Y_i$ denotes the experimental data at $\bar{t}_i$, $\kappa_i$ is a weighting factor of the importance of the point at $\bar{t}$, and N is the number of points from each side of the point at $\bar{t}=0$.

The eight equations to determine the eight coefficients are then obtained by differentiation as $$\frac{\partial E_{rror}}{\partial C_j} = 0, \; j = 1, ... 8 \quad (3)$$

Because the displacement at $\bar{t}=0$ is the sum $C_1+C_3+C_5$, it shows that the displacement consists of $C_1$, the amplitude of the harmonic component $\cos(\omega\bar{t})$, $C_3$, the amplitude of the harmonic component $\cos(2\omega\bar{t})$, and $C_5$, a moving average. Since the amplitudes of the two harmonics ($C_1, C_3$) are not constant, we estimate the effective amplitude at each harmonic by computing the root-mean-square ($\sqrt{2}$RMS). The effective amplitudes of $C_1$ and $C_3$ are designated as $A_1$ and $A_2$, respectively. Because effective amplitudes can be determined for vertical head movement or vertical pelvic movement, the ratios can be designated as $A_{1Head}$ and $A_{2Head}$ for head movement and $A_{1Pelvis}$ and $A_{2Pelvis}$ for pelvis movement. The ratios $A_{1Head}/A_{2Head}$ and $A_{1Pelvis}/A_{2Pelvis}$ represent the severity of lameness in the forelimb and hindlimb, respectively. For example, a greater ratio indicates more severe lameness and a lesser ratio indicates less severe lameness.

In aspects, where the hindlimb sensor 108 is not used, the same equation can be used to determine the ratios $A_{1Head}/A_{2Head}$ and $A_{1Pelvis}/A_{2Pelvis}$. During a walking gait, for example, when the forelimb of the animal is down, the hindlimb (i.e., on the same side) is up, and when the forelimb up, the hindlimb (i.e., on the same side) is down. Moreover, if the vertical position of the forelimb is increasing (i.e., going up) the vertical position of the hind limb is decreasing (i.e., going down), and if the vertical position of the forelimb is decreasing the vertical position of the hind limb is increasing. As such, the vertical position of the hindlimb can be mathematically determined based on the position and direction of vertical movement of the forelimb, as determined from the forelimb sensor 106. According to one aspect, the hindlimb sensor 108 is not needed to detect lameness during the walking gait of the animal.

A curve-modification module 208 is configured to smooth and modify the simulated movement patterns though a user-interactive interface. For example, the user optionally uses the UI 124 to input data to modify the simulated movement patterns of the head or pelvis. For example, the user can use the UI 124 to manually eliminate data points that are deemed erroneous. The curve-modification module 208 receives the user's input and smoothes the simulated movement patterns (i.e., resulting curves) for improved accuracy.

In another aspect, the curve-modification module 208 is configured to automatically identify and eliminate erroneous data points. For example, the curve-modification module 208 processes the data points produced by the curve fitting algorithm to identify data points that would result in a spike and eliminates such data points from the simulated movement patterns, A position-detection module 210 is configured to detect maximum and minimum head and/or pelvic positions during strides along the modified movement patterns. In particular, the maximum and minimum positions of the vertical head and/or pelvis during the animal's movement are determined along the simulated curve first through a Peak-Detection Algorithm. The Peak-Detection Algorithm assigns the first maximum position of the sum of the first and second harmonics as the beginning point for calculating the maximum and minimum differences between the sum of the first and second harmonics as obtained from the aforementioned Data-Decomposition Algorithm. (i.e., equation (1)).

According to another aspect, a user, such as a veterinarian or a clinician, studying the simulated pattern with maximum and minimum data points can decide if the motion data included in the vertical position signals 110, 112 from the head sensor 102 and pelvic sensor 104 should be smoothed (e.g., eliminate spikes from curves) to reduce or to eliminate errors in the Peak-Detection Algorithm. If smoothing is desired, the user can use the UI 124 to identify which segment of the data should be smoothed. The user can also decide if any computer-assigned maximum or minimum data points should be deleted or if any maximum or minimum data points not automatically assigned by the computer should be manually added.

Figure 3:
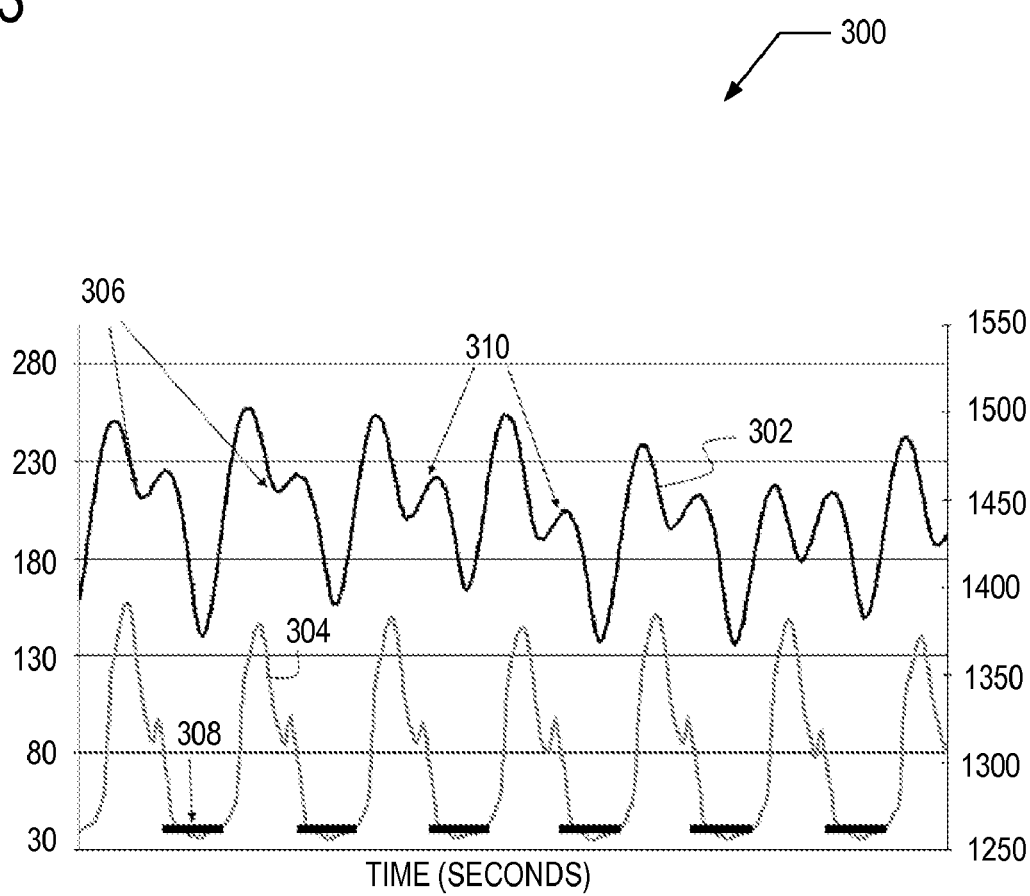
FIG. 3 illustrates a plot of the vertical movement patterns of a head position and a forelimb position for a horse with peak pain of lameness occurring at the time of hoof impact.

FIG. 3 is a plot 300 of the vertical movement pattern of a head (obtained after double integration of the raw vertical head acceleration data) and raw forelimb foot vertical position for a horse with peak pain of lameness occurring at the time of hoof impact. A head pattern curve 302 represents vertical head movement of an affected horse, and a forefoot curve 304 represents vertical right forelimb foot movement. The dips 306 represent less downward movements of the head during the stance phases of the right limb as indicated by reference character 308. The peaks 310 represent less upward movement of the head after the stance phase of the right forelimb.

Referring again to FIG. 2, a phase-shift calculation module 212 identifies an affected limb and determines severity based on the maximum and minimum data points of the head and pelvic vertical positions. According to one aspect, the evaluation system 100 uses four vertical head movement reference patterns that correspond to forelimb lameness and three pelvic reference patterns that correspond to hindlimb lameness. The reference patterns are based on motion data previously measured in a laboratory for animals with natural lameness. The reference patterns are determined by a theoretical summing of first and second harmonics, as determined from a data decomposition algorithm at gradually increasing phase shifts between the harmonics and are compared to the simulated movements patterns to determine the affected limb. The reference patterns have been confirmed in a laboratory setting using data collected from animals with natural lameness conditions.

FIGS. 4A-4D illustrate four reference patterns of head movement that correspond to forelimb lameness. In FIGS. 4A-4D, a first curve 400 represents corrected gross vertical head movement, a second curve 402 represents the first harmonic of head movement or the motion of the head due to lameness, a third curve 404 represents the second harmonic of head movement or natural vertical head movement, and a fourth curve 406 represents the stance phase of the right forelimb.

In one embodiment, the four reference head movement patterns that correspond to forelimb lameness are as follows: 1) Less downward movement of the head during the stance phase of the affected limb and less upward movement of the head after the stance phase of the affected limb occurs when the peak-time-of-lameness is at impact at the beginning of the stance phase of the stride of the affected limb, as illustrated in FIG. 4A; 2) Less downward movement of the head during the stance phase of the affected limb only indicates peak-time-of-lameness at mid-stance when the limb is perpendicular to the ground and the vertical ground reaction forces on the limb are maximal, as illustrated in FIG. 4B; 3) Less downward movement of the head during the stance phase of the affected limb and more upward movement of the head after the stance phase of the affected limb indicates peak-time-of-lameness occurring during the second half of the stance phase of the lame limb (propulsive phase of stance), as illustrated in FIG. 4C; and 4) Only greater upward movement of the head after the stance phase of the affected limb indicates peak-time-of-lameness occurring during breakover (also called pushoff), which is the last part of the stance phase of the limb between heel off and toe off, as illustrated in FIG. 4D.

Figure 5A:
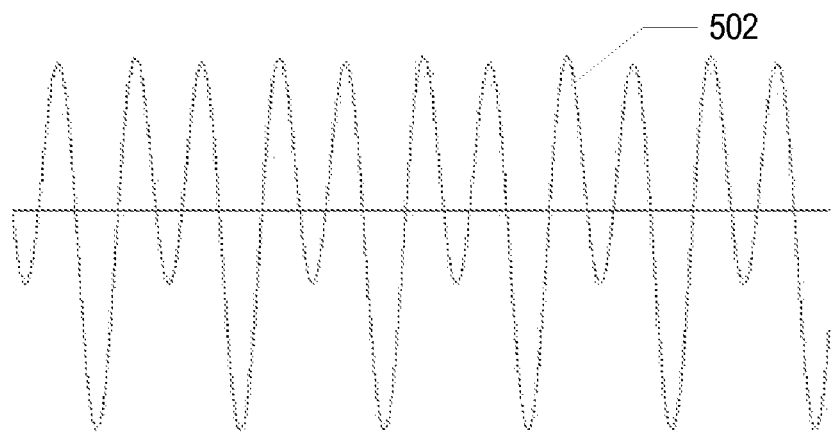
FIGS. 5A-5C illustrate three reference patterns of pelvic movement due to hindlimb lameness.
Figure 5B:
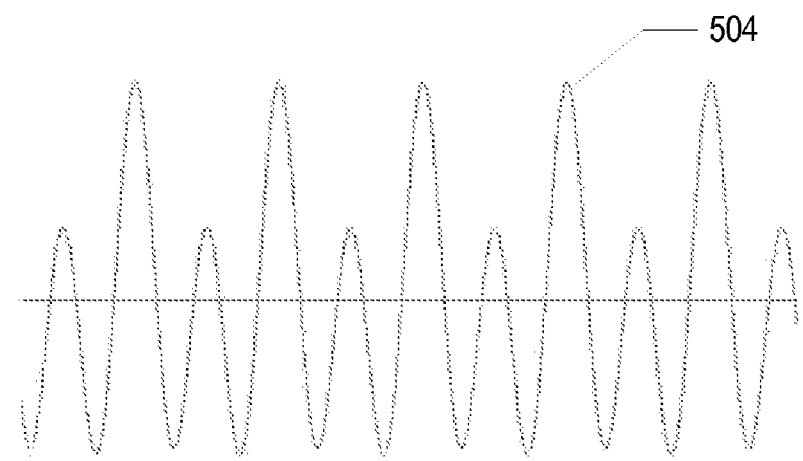
Figure 5C:
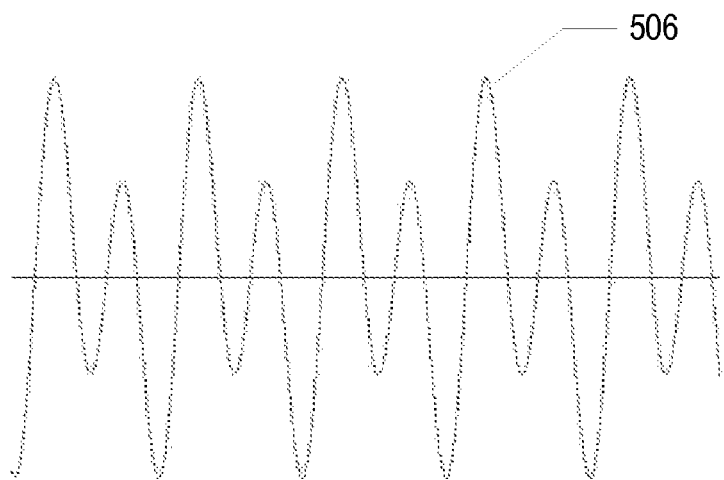

FIGS. 5A-5C illustrate four reference patterns of pelvis movement that correspond to forelimb lameness. In one embodiment, the three reference patterns that correspond to hindlimb lameness are as follows: 1) Less downward movement of the pelvis during the stance phase of the affected limb occurs when the peak-time-of-lameness is during the cranial or deceleratory phase of the stance phase of the stride, as illustrated by plot 502 in FIG. 5A; 2) Less upward movement of the pelvis after the stance phase of the affected limb occurs when the peak-time-of-lameness is in the caudal or acceleratory phase of the stance phase of the stride, as illustrated by plot 504 in FIG. 5B; and 3) Less downward movement of the pelvis during the stance phase of the affected limb and less upward movement of the pelvis after the stance phase of the affected limb occurs when lameness occurs throughout the stance phase of the affected limb, as illustrated by plot 506 in FIG. 5C.

In practice, to identify an affected limb, a user studying the movement pattern with maximum and minimum data points, as illustrated in FIG. 3, identifies the first maximum from the vertical head or vertical pelvic position after a stance phase of a particular limb (e.g., forelimb). The sign (positive or negative) of differences in maximum and minimum positions between right and left stance phases of the stride then determines the affected limb (right versus left).

Referring back to FIG. 2, after identifying the affected limb, the phase shift calculation module 212 performs a peak-time-of-lameness check to determine the type of lameness by calculating differences in the time indexes between the peaks of the first and second harmonics of vertical head or pelvis positions obtained from equation (1) and the above described Peak-Detection Algorithms.

A reporting module 214 is configured to generate output data, such as a report, screen, table, or other data that indicates a result of the analyses, such as a summary of the overall severity of lameness, affected limb(s), and type of lameness for display to the user via the UI 124 or an output device. For example, the reporting module 214 generates reports comprising the summary of the severity of lameness, affected limb(s), and type of lameness for viewing by the user.

In one aspect, the output data is in an electronic format such that it can be viewed via the UI 124. Moreover, such output data can be communicated to one or more remote computers or processing systems via a communication network (not shown), such as the Internet, an intranet, a wireless network, or other networks. In another aspect, the output data is stored on media for transfer to another device. In another aspect, the reports or other output data are in a tangible format such that they can be viewed and physically handled by the user.

Figure 6A:
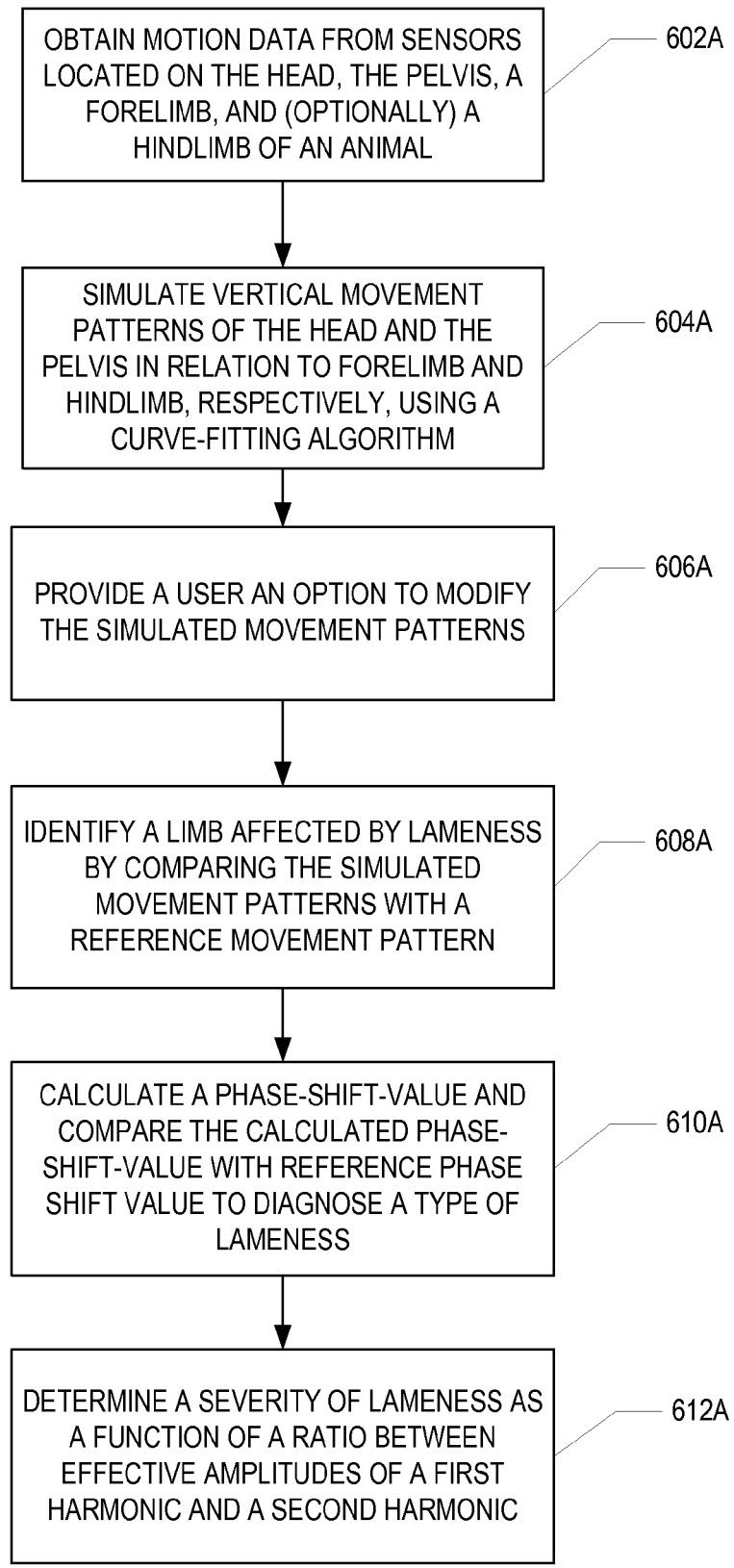
FIG. 6A is a flow chart illustrating a lameness detection method in accordance with an aspect of a lameness evaluation application.

FIG. 6A is a flow diagram illustrating a lameness detection method in accordance with an aspect of the evaluation application 202. At 602A, the evaluation application 202 obtains motion data from sensors located on the head, the pelvis, a forelimb, and a hindlimb of an animal during a period of trotting or walking gait. The motion data from the head and pelvis is considered acceleration data and the motion data from the forelimb and hindlimb is considered gyroscopic data. The evaluation application 202 uses a curve-fitting algorithm to simulate vertical movement patterns of the head in accordance with forelimb movement and to simulate vertical movements of the pelvis in accordance with hindlimb movement during a stride at 604A. The curve-fitting algorithm employs two harmonics and other transient components derived from the motion data. According to one aspect, a first harmonic has a frequency equal to one times (1×) the stride rate and a second harmonic has a frequency equal to two times (2×) the stride rate.

At 606A, the evaluation application 202 provides a user an option to modify the simulated movement patterns. For example, the user is provided the ability to eliminate data points from the motion data that is used to by the curve-fitting algorithm to create the simulated movement patterns. The evaluation application 202 identifies a limb affected by lameness by comparing the simulated movement patterns with a reference movement pattern retrieved from a memory (e.g., memory 126) at 608A. At 610A, the evaluation application 202 diagnoses a type of lameness by calculating a phase-shift-value between the first and second harmonics and comparing the calculated phase-shift-value with the reference phase shift value. The evaluation application 202 determines the severity of lameness in the identified limb as a function of a ratio of a calculated effective amplitude of the first harmonic to a calculated effective amplitude of the second harmonic at 612A.

Figure 6B:
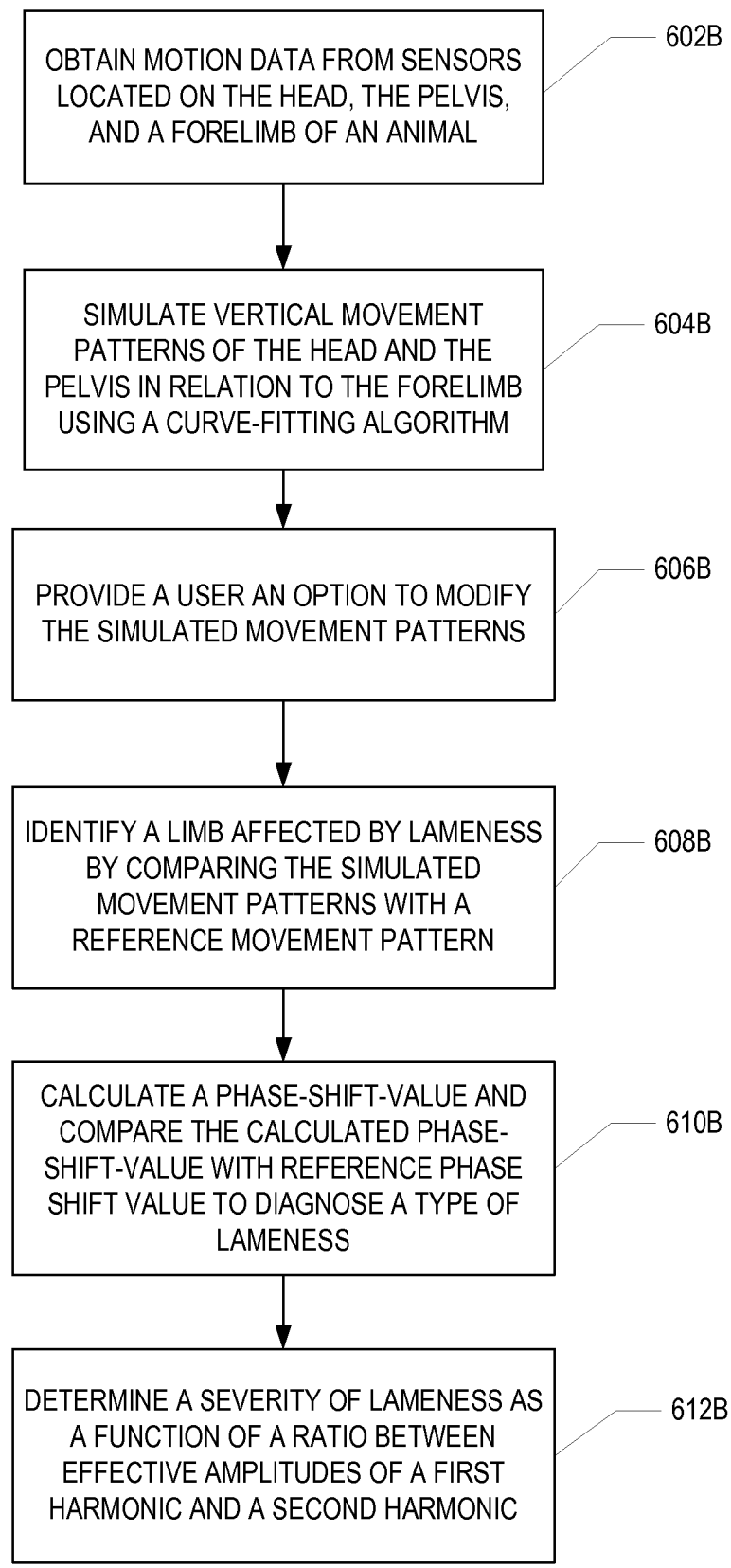
FIG. 6B is another flow chart illustrating a lameness detection method in accordance with an aspect of a lameness evaluation application

FIG. 6B is a flow diagram illustrating a lameness detection method in accordance with another aspect of the evaluation application 202. At 602B, the evaluation application 202 obtains motion data from sensors located on the head, the pelvis, and a forelimb of an animal during a period of trotting or walking gait. The motion data from the head and pelvis is considered acceleration data and the motion data from the forelimb and hindlimb is considered gyroscopic data. The evaluation application 202 uses a curve-fitting algorithm to simulate vertical movement patterns of the head in accordance with forelimb movement and to simulate vertical movements of the pelvis in accordance with forelimb movement during a stride at 604B. The curve-fitting algorithm employs two harmonics and other transient components derived from the motion data. According to one aspect, a first harmonic has a frequency equal to one times (1×) the stride rate and a second harmonic has a frequency equal to two times (2×) the stride rate.

At 606B, the evaluation application 202 provides a user an option to modify the simulated movement patterns. For example, the user is provided the ability to eliminate data points from the motion data that is used to by the curve-fitting algorithm to create the simulated movement patterns. The evaluation application 202 identifies a limb affected by lameness by comparing the simulated movement patterns with a reference movement pattern retrieved from a memory (e.g., memory 126) at 608B. At 610B, the evaluation application 202 diagnoses a type of lameness by calculating a phase-shift-value between the first and second harmonics and comparing the calculated phase-shift-value with the reference phase shift value. The evaluation application 202 determines the severity of lameness in the identified limb as a function of a ratio of a calculated effective amplitude of the first harmonic to a calculated effective amplitude of the second harmonic at 612B.

Figure 7:
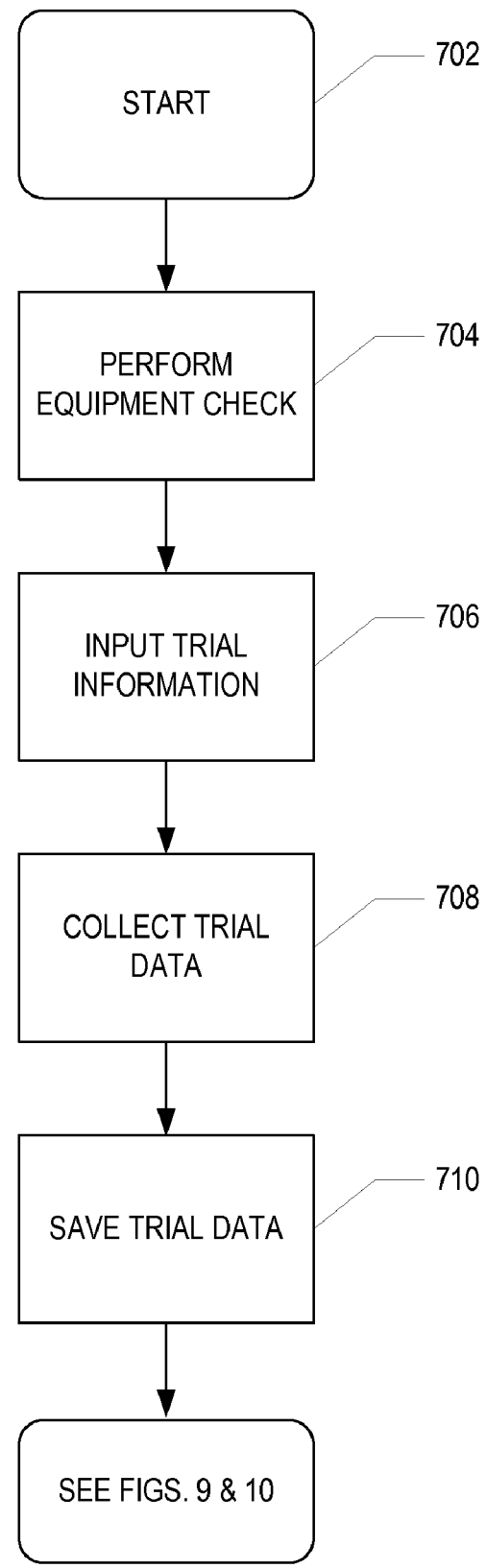
FIG. 7 is a flow chart illustrating a general data acquisition method in accordance with an aspect of a lameness evaluation system.

FIG. 7 illustrates a data acquisition method in accordance with an aspect of the evaluation application 202. At 702, the evaluation application 202 is executed to start data acquisition. At 704, the evaluation application 202 performs an equipment check. For example, the evaluation application 202 performs a test communication with motion sensors (e.g., motion sensors 102-108) to ensure that there is a communication link with each of the sensors. The evaluation application 202 allows a user to input trial information at 706. The trial information is collected at 708, and it is saved to a memory at 710.

Figure 8:
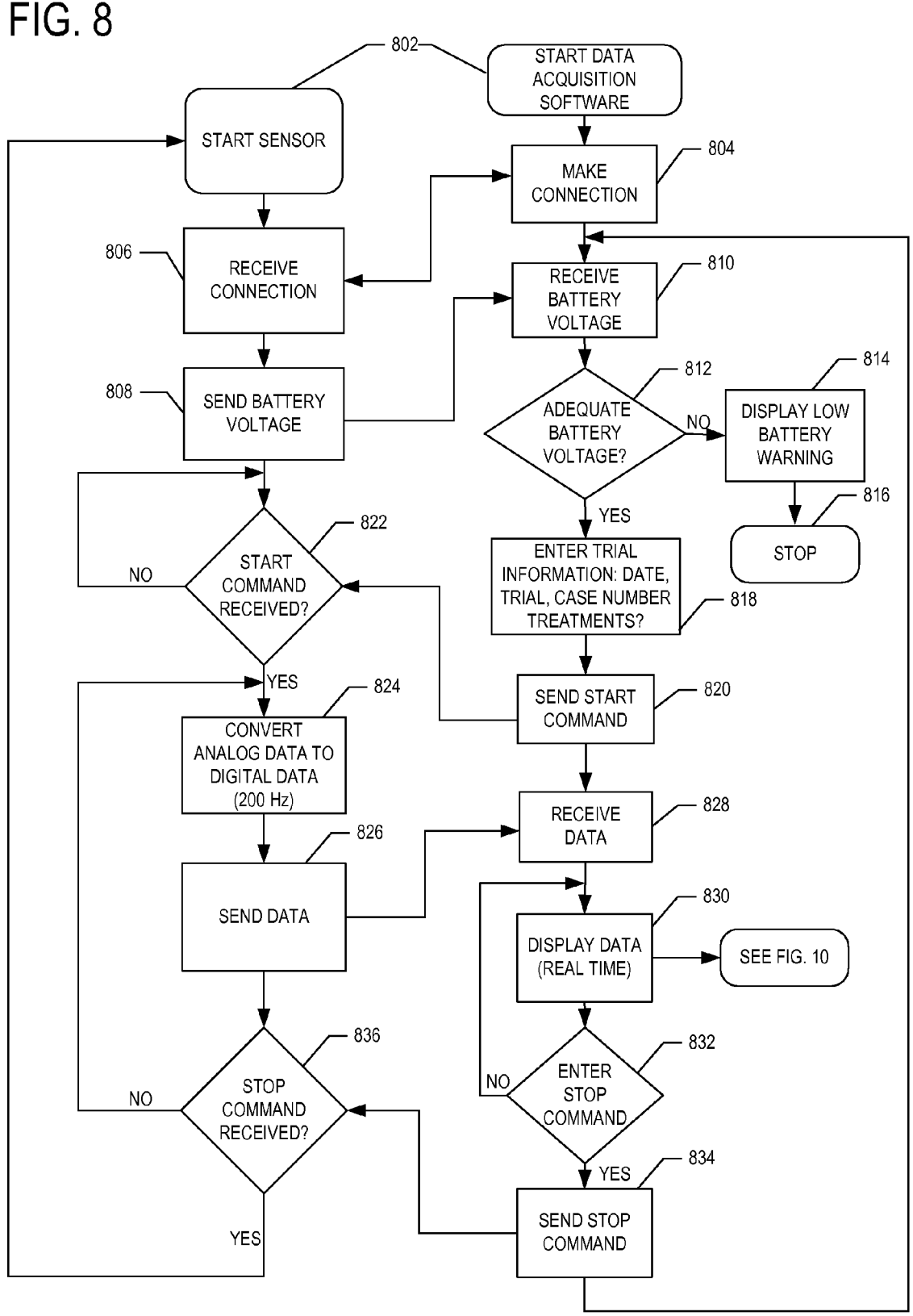
FIG. 8 is a flow chart illustrating a detailed data acquisition method in accordance with an aspect of a lameness evaluation system.

FIG. 8 illustrates details of the data acquisition method in accordance with an aspect of the evaluation application 202. At 802, the evaluation application 202 executes the data acquisition module 204, and the motion sensors outfitted to a head, pelvis, and at least one foot of the animal are activated. A communication signal is sent to the motion sensors to establish a communication connection at 804. At 806, the motion sensors receive the communication signal, and the communication connection is established. The motions sensors send power data, such as a battery voltage level, to the evaluation application 202 at 808. At 810, the evaluation application 202 receives the power data and determines whether there is sufficient power available for operating the sensors at 812. If it is determined that sufficient power is not available at 812, the evaluation application 202 displays a message to a user via the UI 124 warning that there is low power (e.g., low battery) at 814, and execution of the evaluation application 202 is stopped at 816. If sufficient power is available at 812, the evaluation application 202 displays an input form to a user via the UI 124 requesting trial information at 818. For example, the user can enter a date of the trial, a trial case number, and whether there are any treatments.

At 820, the evaluation application 202 sends a start command to the motion sensors to begin collecting and transmitting motion data. At 822, the sensors determine whether the start command signal has been received. If the start command signal has not been received at 822, the sensors continue to monitor for the start command signal. If the start command signal has been received at 822, the sensors convert analog motion data to digital motion data at 824. At 826, the sensors send the digital motion data to the evaluation application 202. The evaluation application 202 begins receiving the digital motion data at 828. At 830, the evaluation application 202 displays motion data values to the user via a user interface (e.g., UI 124) in near real time and stores the motion data values in a memory. According to one aspect, the motion data is stored in the memory as a separate file for each animal from which data is being acquired.

The user can use the UI 124 to generate a stop command to send to the sensors to stop collecting and transmitting motion data at 832. If the user does not generate a stop command at 832, the evaluation application 202 continues to display motion data values to the user via the UI 124 in near real time. If the user generates a stop command at 832, the evaluation application 202 sends the stop command to the sensors at 834.

At 836, the sensors determine whether a stop command signal has been received. If the stop command signal has not been received at 836, the sensors continue to monitor for the stop command signal. If the stop command signal has been received at 836, the sensors stop collecting and transmitting motion data and wait for the next a communication signal to be received at 806.

Figure 9:
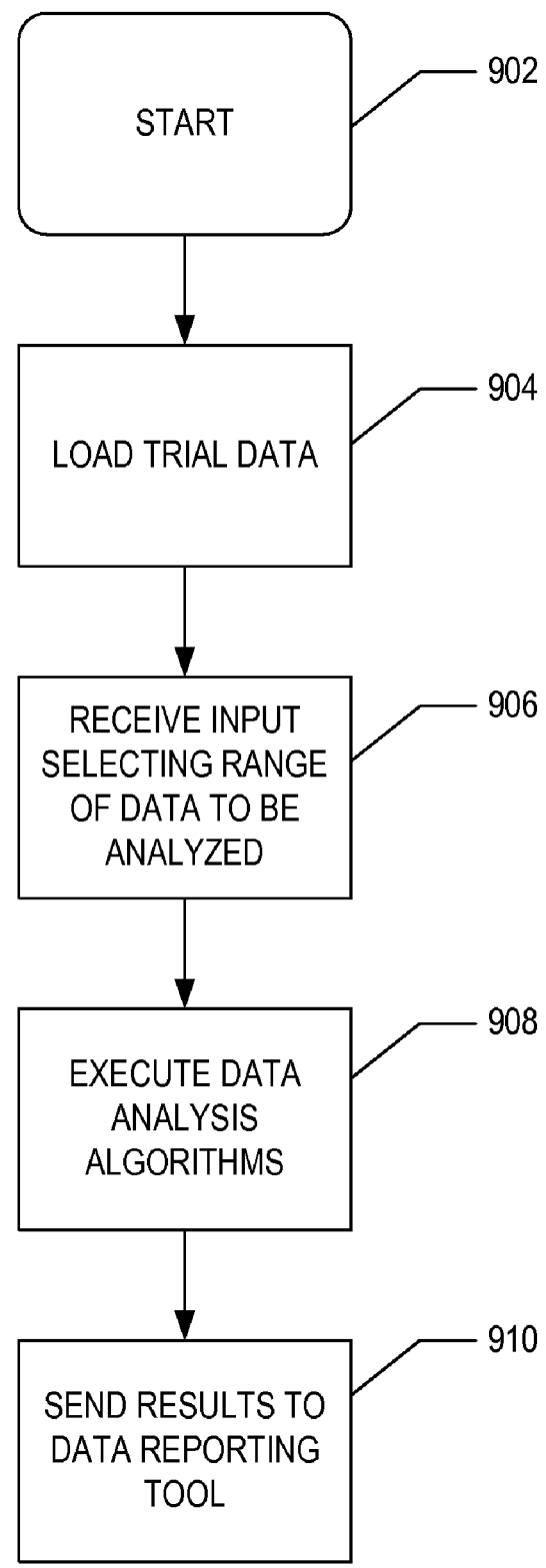
FIG. 9 is a flow chart illustrating a general data analysis method in accordance with an aspect of a lameness evaluation system.

FIG. 9 illustrates a data analysis method in accordance with an aspect of the evaluation application 202. At 902, the evaluation application 202 starts the data analysis. The evaluation application 202 loads trial data from a memory at 904 and retrieves motion data from the memory for analysis at 906. At 908, the evaluation application 202 executes data analysis algorithms. The results obtained from the data analysis algorithms are provided to a reporting module at 910.

FIG. 10 illustrates details of the data analysis method in accordance with an aspect of the evaluation application 202. At 1002, the evaluation application 202 receives a data analysis command from a user. The data analysis command may indicate a specific file that contains motion data for a particular animal for which lameness evaluation is desired. The evaluation application 202 loads the file comprising motion data for the particular animal at 1004. At 1006, the evaluation application 202 plots acceleration data corresponding to vertical head movements and vertical pelvis movements in a graph and displays the graph to the user. The user uses the user interface (e.g., UI 124) to select a desired range of motion data to be analyzed at 1008.

At 1010, the user uses the UI 124 to provide input indicating whether the selected range is accepted. For example, a dialogue box may be displayed to the user via the UI 124 asking whether the user would like to accept the selected range for analysis. If the user does not accept the range at 1010, the user can use the UI 124 to select a different range of motion data to be analyzed at 1008. If the user accepts the range at 1010, the evaluation application 202 performs a double integration, such as described above, of the selected acceleration data at 1012. At 1014, the evaluation application 202 retrieves gyroscopic data corresponding to angular rational movements of the forelimb and optionally the hindlimb of the particular animal.

At 1016, the evaluation application 202 executes a data-decomposition module that employs a data-decomposition algorithm (see equation 1) to derive simulated motion data that corresponds to the vertical head and pelvic movement patterns in accordance with the respective limb movement (e.g., head vs. forefoot and pelvis vs. hindfoot or optionally head vs. forefoot and pelvis vs. forefoot). The simulated head and/or pelvic motion data is reported to a user via a reporting module at 1018.

The evaluation application 202 executes a peak detection algorithm to identify maximum and minimum data positions from of the simulated motion data at 1020. As described above, the peak detection algorithm assigns the sum of the first and second harmonics as obtained from the simulated motions data-decomposition algorithm as the maximum and minimum positions. At 1022, the evaluation application 202 generates a plot (FIG. 3) of the sum of harmonics with assigned maximum and minimum positions.

At 1024, the user uses the UI 124 to provide an input to the evaluation application 202 indicating whether data smoothing is desired. For example, a dialogue box or another input form may be displayed to the user via the UI 124 allowing the user to indicate whether data smoothing is desired. For example, as described above, a user (e.g., veterinarian/clinician) studying the simulated pattern with maximum and minimum positions, such as illustrated in FIG. 3, can determine if the vertical position signals should be smoothed to reduce or eliminate errors in the Peak-Detection Algorithm. If the user provides input indicating that smoothing is desired, the evaluation application 200 allows the user to select a data segment for smoothing at 1026 and smoothes the selected data segment at 1028. The evaluation application 202 then executes the peak detection algorithm to identify the maximum and minimum positions of the smoothed motion data at 1020.

If the user provides input indicating that smoothing is not desired at 1024, the user can use the UI 124 to provide an input to the evaluation application 202 indicating whether maximum and minimum data points should be added to or deleted from the motion data at 1030. For example, a different dialogue box may be displayed to the user via the UI 124 allowing the user to indicate a desire to add or to delete maximum and/or minimum data points. If the user provides input indicating a desire to add or to delete maximum and/or minimum data points, the evaluation application 202 allows the user to select a data segment at 1032, to select an add option or to select a delete option at 1034, and to select a maximum or minimum data point at 1036. At 1038, the evaluation application 202 adds or deletes the selected maximum and/or selected minimum as indicated by user selections at 1032, 1034, and 1036.

If the user provides input to the evaluation application 202 indicating the maximum and/or minimum data points should not be added to or deleted from the motion data at 1030, the user can use the UI 124 to provide an input to define a first head position maximum at 1040. The evaluation application 202 calculates a maximum and minimum difference between the first head position defined by the user and the maximum and minimum positions determined by the peak detection algorithm at 1042. The calculated maximum and minimum difference can be used to identify a limb affected with lameness. For example, by comparing the calculated maximum and minimum differences to maximum and minimum differences obtained from reference movement patterns (e.g., FIGS. 4A-4D and FIGS. 5A-5C) that correspond to forelimb lameness and hindlimb lameness, the affected limb can be identified. The evaluation application 202 further calculates the phase shift between harmonics at 1044. The calculated phase shift is used to determine a type of lameness. For example, the calculated phase shift is compared to various reference phase shift values that correspond to a different type of lameness to identify the type of lameness. The calculated maximum and minimum differences and the calculated phase shift are reported to a user via a reporting module at 1018.

As various changes could be made in the above constructions, systems, and methods without departing from the scope of aspects of the invention, it is intended that all matter contained in the above description and shown in the accompanying drawings shall be interpreted as illustrative and not in a limiting sense.

What is claimed is:

1. A system for evaluating lameness in a four-legged animal comprising:
    a plurality of motion sensors configured to generate a corresponding plurality of signals comprising motion data representative of a head motion, a pelvis motion, and at least one limb motion during a stride of the animal; and
    a processing system configured to receive the plurality of signals during the stride via wireless communication and to receive input data, the processing system comprising an evaluation application comprising:
        a data-acquisition module configured to retrieve motion data from the received plurality of signals;
        a data-decomposition module configured to:
            determine a first harmonic component comprising a first frequency, the first harmonic corresponding to a unilateral lameness contribution to a vertical movement of the at least one limb motion;
            determine a second harmonic component with a second frequency, the second harmonic corresponding to a normal, biphasic, vertical movement of the at least one limb motion;
            determine a low-frequency transient component corresponding to an extraneous vertical head movement or to an extraneous pelvis movement; and
            generate a simulated head movement pattern and a simulated pelvis movement pattern for the stride based on the determined first harmonic, the determined second harmonic component, and the determined low-frequency transient component;
        a curve-modification module configured to modify and smooth the simulated head and pelvis movement patterns based on the input data;
        a position-detection module configured to detect a maximum head position, a minimum head position, a maximum pelvis position, and a minimum pelvis position during the stride based on the modified simulated head and pelvis movement pattern; and
        a phase-shift calculation module configured to:
            identify a limb affected with lameness based on a comparison of the detected maximum head position, the detected minimum head position, the detected maximum pelvis position, and the detected minimum pelvis position with at least one reference pattern, the at least one lameness reference pattern indicating a peak time of lameness; and
            determine a phase-shift between the first harmonic component and the second harmonic component and to determine a type of lameness based on the determined phase-shift.

2. The system of claim 1 wherein the plurality of sensors comprise:
   a head sensor configured to generate a first signal comprising first motion data representative of the head motion;
   a pelvis sensor configured to generate a second signal comprising second motion data representative of the pelvis motion; and
   a forelimb sensor configured to generate a third signal comprising third motion data representative of a forelimb motion.

3. The system of claim 2 wherein the plurality of sensors further comprise a hindlimb sensor configured to generate a fourth signal comprising fourth motion data representative of a hindlimb motion.

4. The system of claim 1 further comprising a reporting module configured to generate a report comprising a summary of the affected limb, a type of lameness, and a severity of lameness.

5. The system of claim 1 wherein the data-acquisition module is further configured to retrieve the motion data at a predefined interval.

6. The system of claim 5 wherein the predefined interval comprises a user defined time period.

7. The system of claim 1 wherein head motion data and pelvis motion data correspond to acceleration data, wherein limb motion data corresponds to gyroscopic data, and wherein the data-decomposition module is configured to generate the simulated vertical head and pelvis movement patterns by:
   double integrating the acceleration data corresponding to the head motion and the pelvis motion;
   calculating a first stride rate component corresponding to the head motion as a function of the gyroscopic data for a forelimb motion;
   calculating a second stride rate component corresponding to the pelvis motion as a function of the gyroscopic data for a hindlimb motion; and
   employing a curve-fitting algorithm to generate the simulated vertical head movement pattern and the simulated pelvis movement pattern as a function of the double integrated acceleration data, the first stride rate component, and the second stride rate component.

8. The system of claim 1 wherein the input data identifies at least one motion data point deemed erroneous by the user, and wherein the curve-modification module eliminates the identified at least one motion data point to smooth the simulated vertical head and pelvis movement patterns.

9. The system of claim 1 wherein the curve-modification module is further configured to automatically identify at least one erroneous motion data point and to automatically eliminate the at least one erroneous motion data point to smooth the simulated vertical head and pelvis movement patterns.

10. The system of claim 1 wherein the phase-shift calculation module is further configured to:
    calculate a first effective amplitude of the first harmonic component and to calculate a second effective amplitude of the second harmonic component; and
    determine a severity of lameness in the identified limb as a function of a ratio of the first effective amplitude to the second effective amplitude.

11. The system of claim 1 wherein the at least one lameness reference pattern comprises four vertical head movement reference patterns with forelimb lameness and three vertical pelvis movement reference patterns with hindlimb lameness.

12. The system of claim 11 wherein the four vertical head movement reference patterns comprise:

a first vertical head pattern depicting less downward movement of a head of the animal during a stance phase of an affected forelimb and less upward movement of the head after the stance phase of the affected forelimb, the first vertical head pattern corresponding to a peak-time-of-lameness occurring at impact at a beginning of the stance phase of the stride of the affected forelimb;
   a second vertical head pattern depicting less downward movement of the head during the stance phase of the affected forelimb, the second vertical head pattern corresponding to the peak-time-of-lameness occurring at mid-stance when the affected forelimb is perpendicular to a ground level and vertical ground reaction forces on the affected forelimb are maximal;
   a third vertical head position pattern depicting less downward movement of the head during the stance phase of the affected forelimb and more upward movement of the head after the stance phase of the affected forelimb, the third vertical head position pattern corresponding to the peak-time-of-lameness occurring during a second half of the stance phase of the forelimb; and
   a fourth vertical head position pattern only depicting a greater upward movement of the head after the stance phase of the affected forelimb, the fourth vertical head position pattern corresponding to the peak-time-of-lameness occurring during a push off.

13. The system of claim 11 wherein the three vertical pelvis movement reference patterns for hindlimb lameness comprise:
    a first vertical pelvis pattern depicting less downward movement of a pelvis of the four-legged animal during a stance phase of an affected hindlimb, the first vertical pelvis pattern corresponding to a peak-time-of-lameness occurring during a deceleratory phase of the stance phase of the affected hindlimb;
    a second vertical pelvis pattern depicting less upward movement of the pelvis after the stance phase of the affected hindlimb, the second vertical pelvis pattern corresponding to the peak-time-of-lameness occurring during an acceleratory phase of the stance phase of the of the affected hindlimb; and
    a third vertical pelvis pattern depicting less downward movement of the pelvis during the stance phase of the affected hindlimb and less upward movement of the pelvis after the stance phase of the affected hindlimb, the third vertical pelvis pattern corresponding to the peak-time-of lameness occurring when lameness occurs throughout the stance phase of the affected hindlimb.

14. The system of claim 1 wherein the at least one limb motion comprises at least one foot motion.

15. An evaluation system for evaluating lameness in an animal and operable with at least one processor, the evaluation system configured to receive a plurality of signals comprising motion data representative of a head motion, a pelvis motion, and at least one limb motion during a stride of the animal, the evaluation system comprising:
    a data-acquisition module configured to collect motion data from the received plurality of signals;
    a data-decomposition module configured to:
       determine a first harmonic component comprising a first frequency, the first harmonic corresponding to a unilateral lameness contribution to a vertical movement of the at least one limb motion;
       determine a second harmonic component with a second frequency, the second harmonic corresponding to a normal, biphasic, vertical movement of the at least one limb motion;

determine a low-frequency transient component corresponding to an extraneous vertical head movement or to an extraneous pelvis movement; and generate simulated head and pelvis movement patterns for the stride based on the determined first harmonic, the determined second harmonic component, and the determined low-frequency transient component;

a curve-modification module configured to receive input data and to modify and smooth the simulated head and pelvis movement patterns based on input data;

a position-detection module configured to detect a maximum head position, a minimum head position, a maximum pelvis position, and a minimum pelvis position during the stride based on the modified simulated head and pelvis movement patterns; and a phase-shift calculation module configured to:
identify a limb affected with lameness based on a comparison of the detected maximum head position, the detected minimum head position, the detected maximum pelvis position, and the detected minimum pelvis position with at least one lameness reference pattern, the at least one lameness pattern indicating a peak time of lameness; and determine a phase-shift between the first harmonic component and the second harmonic component and to determine a type of lameness based on the determined phase-shift.

16. The system of claim 15 wherein the evaluation system comprises a plurality of sensors configured to generate the plurality of signals comprising:
a head sensor configured to generate a first signal comprising first motion data representative of the head motion;
a pelvis sensor configured to generate a second signal comprising second motion data representative of the pelvis motion; and
a forelimb sensor configured to generate a third signal comprising third motion data representative of a forelimb motion.

17. The system of claim 16 wherein the plurality of sensors further comprise a hindlimb sensor configured to generate a fourth signal comprising fourth motion data representative of a hindlimb motion.

18. The system of claim 15 further comprising a reporting module configured to generate output data comprising a summary of the affected limb, a type of lameness, and a severity of lameness.

19. The system of claim 15 wherein the data-acquisition module collects the motion data at a predefined interval.

20. The system of claim 19 wherein the predefined interval comprises a user defined time period.

21. The system of claim 15 wherein head motion data and pelvis motion data correspond to acceleration data, wherein limb motion data corresponds to gyroscopic data, and wherein the data-decomposition module is configured to generate the simulated vertical head and pelvis movement patterns by:
double integrating the acceleration data corresponding to the head motion and the pelvis motion;
calculating a first stride rate component corresponding to the head motion as a function of the gyroscopic data for a forefoot motion;
calculating a second stride rate component corresponding to the pelvis motion as a function of the gyroscopic data for a hind foot motion; and
employing a curve-fitting algorithm to generate the simulated vertical head movement pattern and the simulated pelvis movement pattern as a function of the double integrated acceleration data, the first stride rate component, and the second stride rate component.

22. The system of claim 15 wherein the input data identifies at least one missing motion data point or at least one erroneous motion data point, and wherein the curve-modification module is configured to add the identified at least one missing motion data point and to eliminate the identified at least one erroneous motion data point from the simulated vertical head and pelvis movement patterns.

23. The system of claim 15 wherein:
the phase-shift calculation module is further configured to:
calculate a first effective amplitude of the first harmonic component and to calculate a second effective amplitude of the second harmonic component, and
determine a severity of lameness in the identified limb as a function a ratio of the first effective amplitude to the second effective amplitude.

24. The system of claim 15 wherein the at least one lameness reference pattern comprises four vertical head movement reference patterns with forelimb lameness and three vertical pelvis movement reference patterns with hindlimb lameness.

25. The system of claim 24 wherein the four vertical head movement reference patterns comprise:
a first vertical head pattern depicting less downward movement of a head of the four-legged animal during a stance phase of an affected forelimb and less upward movement of the head after the stance phase of the affected forelimb, the first vertical head pattern corresponding to a peak-time-of-lameness occurring at impact at a beginning of the stance phase of the stride of the affected forelimb;
a second vertical head pattern depicting less downward movement of the head during the stance phase of the affected forelimb, the second vertical head pattern corresponding to the peak-time-of-lameness occurring at a mid-stance when the affected forelimb is perpendicular to a ground level vertical ground reaction forces on the affected forelimb are maximal;
a third vertical head position pattern depicting less downward movement of the head during the stance phase of the affected forelimb and more upward movement of the head after the stance phase of the affected forelimb, the third vertical head position pattern corresponding to the peak-time-of-lameness occurring during a second half of the stance phase of the forelimb; and
a fourth vertical head position pattern depicting a greater upward movement of the head after the stance phase of the affected forelimb, the fourth vertical head position pattern corresponding to the peak-time-of-lameness occurring during a push off.

26. The system of claim 24 wherein the three vertical pelvis movement reference patterns for hindlimb lameness comprise:
a first vertical pelvis pattern depicting less downward movement of a pelvis of the four-legged animal during a stance phase of an affected hindlimb, the first vertical pelvis pattern corresponding to a peak-time-of-lameness occurring during a deceleratory phase of the stance phase of the affected hindlimb;
a second vertical pelvis pattern depicting less upward movement of the pelvis after the stance phase of the affected hindlimb, the second vertical pelvis pattern corresponding to the peak-time-of-lameness occurring during an acceleratory phase of the stance phase of the of the affected hindlimb; and a third vertical pelvis pattern depicting less downward movement of the pelvis during the stance phase of the affected hindlimb and less upward movement of the pelvis after the stance phase of the affected hindlimb, the third vertical pelvis pattern corresponding to the peak-time-of lameness occurring when lameness occurs throughout the stance phase of the affected hindlimb.

27. A computerized method for evaluating lameness in a four-legged animal comprising:
generating a plurality of signals representative of a motion of a head, a pelvis, and at least one limb during a stride of the animal;
receiving the plurality of signals during the stride via wireless communication at a processing system;
collecting motion data from the received plurality of signals;
determining a first harmonic component comprising a first frequency, the first harmonic corresponding to a unilateral lameness contribution to a vertical movement of the at least one limb motion;
determining a second harmonic component with a second frequency, the second harmonic corresponding to a normal, biphasic, vertical movement of the at least one limb motion;
determining a low-frequency transient component corresponding to an extraneous vertical head movement or to an extraneous pelvis movement;
generating simulated head and pelvis movement patterns for the stride based on the determined first harmonic, the determined second harmonic component, and the determined low-frequency transient component;
identifying at least one motion data point to add or to eliminate from the simulated head and pelvis movement patterns;
modifying the simulated head and pelvis movement patterns by eliminating identifying at least one motion data point;
detecting a maximum head position, a minimum head position, a maximum pelvis position, and a minimum pelvis position based on the modified simulated head and pelvis movement patterns;
identifying a limb affected with lameness based on a comparison of the detected maximum head position, the detected minimum head position, the detected maximum pelvis position, and the detected minimum pelvis position with at least one lameness reference pattern, the at least one lameness pattern indicating a peak time of lameness;
calculating a phase-shift between the first harmonic component and the second harmonic component; and
determining a type of lameness based on the determined phase-shift.

28. The method of claim 27 wherein generating the plurality of signals comprises:
generating a first signal at a first sensor, the first signal comprising first motion data representative of the head motion;
generating a second signal at a second sensor, the second signal comprising second motion data representative of the pelvis motion; and
generating a third signal at a third sensor, the third signal comprising third motion data representative of a forelimb motion.

29. The method of claim 28 further comprising generating a fourth signal at a fourth sensor, the fourth signal comprising fourth motion data representative of a hindlimb motion.

30. The method of claim 27 further comprising generating output data comprising a summary identifying the affected limb, a type of lameness, and a severity of lameness.

31. The method of claim 27 wherein the processing further comprises collecting the motion data at a predefined interval.

32. The method of claim 31 wherein the predefined interval comprises a user defined time period.

33. The method of claim 27 wherein head motion data and pelvis motion data correspond to acceleration data, wherein limb motion data corresponds to gyroscopic data, and wherein generating simulated vertical head and pelvis movement patterns comprises:
double integrating the acceleration data corresponding to the head motion and the pelvis motion;
calculating a first stride rate component corresponding to the head motion as a function of the gyroscopic data for a forelimb motion;
calculating a second stride rate component corresponding to the pelvis motion as a function of the gyroscopic data for a hindlimb motion; and
employing a curve-fitting algorithm to generate the simulated vertical head movement pattern and the simulated pelvis movement pattern as a function of the double integrated acceleration data, the first stride rate component, and the second stride rate component.

34. The method of claim 27 wherein the input data is received from the user via a user interface.

35. The method of claim 27 further comprising:
calculating a first effective amplitude of the first harmonic component and calculating a second effective amplitude of the second harmonic component; and
determining a severity of lameness in the identified limb as a function of a ratio of the first effective amplitude to the second effective amplitude.

36. The method of claim 27 wherein the at least one lameness reference pattern comprises four vertical head movement reference patterns with forelimb lameness and three vertical pelvis movement reference patterns with hindlimb lameness.

37. The method of claim 36 wherein the four vertical head movement reference patterns comprise:
a first vertical head pattern depicting less downward movement of a head of the four-legged animal during a stance phase of an affected forelimb and less upward movement of the head after the stance phase of the affected forelimb, the first vertical head pattern corresponding to a peak-time-of-lameness occurring at impact at a beginning of the stance phase of the stride of the affected forelimb;
a second vertical head pattern depicting less downward movement of the head during the stance phase of the affected forelimb, the second vertical head pattern corresponding to the peak-time-of-lameness occurring at a mid-stance when the affected forelimb is perpendicular to a ground level and vertical ground reaction forces on the affected forelimb are maximal;
a third vertical head position pattern depicting less downward movement of the head during the stance phase of the affected forelimb and more upward movement of the head after the stance phase of the affected forelimb, the third vertical head position pattern corresponding to the peak-time-of-lameness occurring during the second half of the stance phase of the forelimb; and
a fourth vertical head position pattern only depicting a greater upward movement of the head after the stance phase of the affected forelimb, the fourth vertical head position pattern corresponding to the peak-time-of-lameness occurring during a push off.

38. The method of claim 36 wherein the three vertical pelvis movement reference patterns for hindlimb lameness comprise:
- a first vertical pelvis pattern depicting less downward movement of a pelvis of the four-legged animal during a stance phase of an affected hindlimb, the first vertical pelvis pattern corresponding to a peak-time-of-lameness occurring during a deceleratory phase of the stance phase of the affected hindlimb;
- a second vertical pelvis pattern depicting less upward movement of the pelvis after the stance phase of the affected hindlimb, the second vertical pelvis pattern corresponding to the peak-time-of-lameness occurring during an acceleratory phase of the stance phase of the of the affected hindlimb; and
- a third vertical pelvis pattern depicting less downward movement of the pelvis during the stance phase of the affected hindlimb and less upward movement of the pelvis after the stance phase of the affected hindlimb, the third vertical pelvis pattern corresponding to the peak-time-of lameness occurring when lameness occurs throughout the stance phase of the affected hindlimb.

39. The method of claim 27 wherein the at least one limb comprises at least one foot.

* * * * *